(12) United States Patent
Watanabe

(10) Patent No.: US 7,889,843 B2
(45) Date of Patent: Feb. 15, 2011

(54) RADIOGRAPHIC APPARATUS

(75) Inventor: Tetsuo Watanabe, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 54 days.

(21) Appl. No.: 12/303,426

(22) PCT Filed: Jul. 5, 2007

(86) PCT No.: PCT/JP2007/063866
§ 371 (c)(1),
(2), (4) Date: Dec. 4, 2008

(87) PCT Pub. No.: WO2008/007721
PCT Pub. Date: Jan. 17, 2008

(65) Prior Publication Data
US 2009/0154648 A1 Jun. 18, 2009

(30) Foreign Application Priority Data
Jul. 10, 2006 (JP) .............................. 2006-188863
May 29, 2007 (JP) .............................. 2007-141491

(51) Int. Cl.
H05G 1/58 (2006.01)
H05G 1/64 (2006.01)
(52) U.S. Cl. ...................... 378/116; 378/98.8; 378/189; 250/370.09
(58) Field of Classification Search ................ 378/98.8, 378/116, 117, 189; 250/370.09
See application file for complete search history.

(56) References Cited

U.S. PATENT DOCUMENTS

| 5,773,832 | A  | * | 6/1998 | Sayed et al. ........... 250/370.09 |
| 6,302,580 | B1 | * | 10/2001 | Dwyer et al. ............... 378/197 |
| 6,859,521 | B2 | * | 2/2005 | Spahn ....................... 378/117 |
| 7,078,703 | B2 | * | 7/2006 | Watanabe ............... 250/370.15 |
| 7,239,685 | B2 | * | 7/2007 | Petrick et al. ............... 378/116 |
| 7,324,628 | B2 | * | 1/2008 | Liu et al. .................... 378/117 |
| 7,343,001 | B2 | * | 3/2008 | Abu Tabanjeh ............. 378/116 |
| 7,365,337 | B2 | * | 4/2008 | Tsuchino et al. ........ 250/370.09 |
| 7,426,261 | B2 | * | 9/2008 | Spahn ....................... 378/98.8 |
| 7,550,733 | B2 | * | 6/2009 | Endo et al. ............ 250/370.09 |
| 7,629,587 | B2 | * | 12/2009 | Yagi et al. ............. 250/370.15 |
| 2006/0070384 | A1 | * | 4/2006 | Ertel ............................ 62/3.3 |
| 2007/0029492 | A1 | * | 2/2007 | Abe ...................... 250/370.09 |
| 2007/0116180 | A1 | * | 5/2007 | Omernick et al. ........... 378/116 |

(Continued)

FOREIGN PATENT DOCUMENTS

DE 102004022804 9/2005

(Continued)

OTHER PUBLICATIONS

EP Search Report in Application No. 07790670.9 issued Sep. 10, 2010.

Primary Examiner—Edward J Glick
Assistant Examiner—Thomas R Artman
(74) Attorney, Agent, or Firm—Fitzpatrick, Cella, Harper & Scinto

(57) ABSTRACT

In order to improve the reliability of a radiographic image detection unit and the reliability of a radiographic apparatus, when it is not detected that the radiographic image detection unit is mounted on a support portion or a cooling portion, processing for restricting radiography of a moving image is executed.

7 Claims, 13 Drawing Sheets

U.S. PATENT DOCUMENTS

| | | | |
|---|---|---|---|
| 2007/0165783 A1* | 7/2007 | Abu Tabanjeh | 378/116 |
| 2008/0054182 A1* | 3/2008 | Yokoyama et al. | 250/370.09 |
| 2009/0010394 A1 | 1/2009 | Watanabe | 378/145 |
| 2010/0044573 A1* | 2/2010 | Yagi et al. | 250/370.08 |

FOREIGN PATENT DOCUMENTS

| | | |
|---|---|---|
| EP | 0920241 | 6/1999 |
| EP | 1537825 | 6/2005 |
| JP | 11-271454 | 10/1999 |
| JP | 2000-037374 | 2/2000 |
| JP | 2002-336225 | 11/2002 |
| JP | 2005-000370 | 1/2005 |

* cited by examiner

RADIOGRAPHIC APPARATUS

TECHNICAL FIELD

The present invention relates to a radiographic apparatus using, for example, a flat panel sensor.

BACKGROUND ART

Conventionally, apparatuses which apply radiation to targets, detect the intensity distributions of radiation transmitted through the targets, and obtain radiographic images of the targets have been widely and generally used in the fields of industrial nondestructive testing and medical diagnosis. As a general method for such radiography, a film/screen method using radiation is available. This is the method of performing radiography by using a combination of a photosensitive film and a phosphor having sensitivity to radiation.

In this method, rare-earth phosphor sheets which emit light upon application of radiation are held in tight contact with the two surfaces of a photosensitive film, and the phosphor sheets convert radiation transmitted through a subject to be radiographed into visible light. The latent image formed on the photosensitive film by making it capture this visible light is then developed, thereby visualizing a radiographic image.

With the recent advances in digital technology, the scheme of playing back the visible image obtained by processing the electrical signal obtained by converting a radiographic image on a CRT or the like has become widespread.

This method temporarily stores a transmission image of radiation as a latent image in a phosphor. There has been proposed a radiographic image recording/playback system which photoelectrically reads out the latent image as a visible image by applying exciting light such as a laser beam to the phosphor. In addition, with the recent advances in semiconductor process technology, an apparatus for capturing a radiographic image in the same manner by using a semiconductor sensor has been developed.

These systems have very wide dynamic ranges as compared with a conventional radiographic system using a photosensitive film, and can obtain a radiographic image which is robust against the influences of variations in the amount of radiation exposure. At the same time, unlike the conventional photosensitive film scheme, this method need not perform any chemical treatment and can instantly obtain an output image.

FIG. 13 is a view showing the arrangement of a radiographic system using the above semiconductor sensor. A radiographic apparatus 2 mounted on a radiographic stand 1 includes a radiation sensor 3 as a semiconductor sensor having a detection surface on which a plurality of photoelectric conversion elements are two-dimensionally arranged.

The phosphor placed on the radiation sensor 3 converts the radiation applied from a radiation generator 4 to a subject S into visible light, and the radiation sensor 3 images the light. A control unit 5 performs digital image processing for the electrical signal output from the radiation sensor 3. A monitor 6 then displays a radiographic image of the subject S on the basis of this processed image signal.

This radiographic system allows the operator to instantly observe an image. The detection panel of such a radiographic system is mounted on a holder specialized for a radiographic form such as radiography in a standing position or a resting position, and is selectively used as needed. This system is stationarily installed in a radiation room. Recently, a portable detection unit has been developed, and is used when it is necessary to radiograph a subject in an arbitrary radiographic posture.

Such a radiographic apparatus is electronic equipment, and hence includes many electronic parts indispensable to digitization, which inevitably pose the problem of heat generation, as compared with the conventional film/screen method. For this reason, it is necessary to efficiently dissipate heat from these electronic parts. Heat dissipation is very important to prevent a change in the characteristics of a radiation detector due to a rise in temperature inside the radiographic apparatus as well as to improve the normal operation and durability of the electronic parts which generate heat.

In addition, it is necessary to suppress a rise in the temperature of the outer jacket of the radiographic apparatus from the viewpoint of the safety of subjects in the field of medical equipment. As indicated by "Japanese Industrial Standard on Safety Standards for Electrical Medical Apparatus (JIS T0601-1)", there is a restriction on the surface temperature of a portion with which a subject comes into contact.

Note that Japanese Patent Laid-Open No. 2000-37374 discloses an apparatus having a cooling mechanism of cooling the heat generated by a detection unit by drawing air through a vacuum port and circulating the air around the detection unit by driving a cooling fan. Japanese Patent Laid-Open No. 2005-370 discloses an apparatus having a cooling mechanism of switching heat dissipation paths to effectively dissipate heat in accordance with an installation form, for example, a standing position or a resting position.

There are demands for the application of a detection unit having a cooling mechanism like that described above to a radiographic apparatus for radiographic moving image. In the case of a radiographic moving image, since radiography is continuously performed, the amount of heat generated increases as compared with conventional radiography of a still image. That is, it is necessary to further improve the cooling performance.

There has also been a radiographic apparatus which independently uses a detection unit detachable from a holder as a cassette type unit instead of a stationary type unit. When this apparatus is to obtain radiographic moving image, in order to improve the cooling performance as described above, it is necessary to mount a new cooling mechanism in the detection unit. This reduces the merit of the compact, lightweight detection unit. In addition, in the case of a radiographic moving image, since the dose of X-rays increases, it is necessary to improve safety.

DISCLOSURE OF INVENTION

It is an object of the present invention to provide a radiographic apparatus which can control processing for a radiographic image in accordance with a radiographic form.

It is another object of the present invention to improve the reliability of a radiographic image detection unit and the safety of a radiographic apparatus in accordance with a radiographic form.

In order to achieve at least one of the above objects, an embodiment of the present invention uses the arrangement of a radiographic apparatus comprising:

a mount detection unit which detects whether a radiographic image detection unit is mounted on a support portion for supporting the radiographic image detection unit; and a controller which executes processing for restricting radiography of a moving image by the radiographic image detection unit when the mount detection unit does not detect mounting of the radiographic image detection unit on the support portion.

According to another aspect, the embodiment uses the arrangement of a radiographic apparatus comprising:

a radiographic image detection unit which acquires a radiographic image;

a mount detection unit which detects whether the radiographic image detection unit is mounted on a cooling portion for cooling the radiographic image detection unit; and a controller which executes processing for restricting radiography of a moving image by the radiographic image detection unit when the mount detection unit does not detect mounting of the radiographic image detection unit on the cooling portion.

Further features of the present invention will become apparent from the following description of exemplary embodiments with reference to the attached drawings.

BRIEF DESCRIPTION OF DRAWINGS

The accompanying drawings, which are incorporated in and constitute a part of the specification, illustrate embodiments of the invention and, together with the description, serve to explain the principles of the invention.

BEST MODE FOR CARRYING OUT THE INVENTION

The preferred embodiments of the present invention will be described in detail with reference to FIGS. 1 to 12.

First Embodiment

Figure 1:
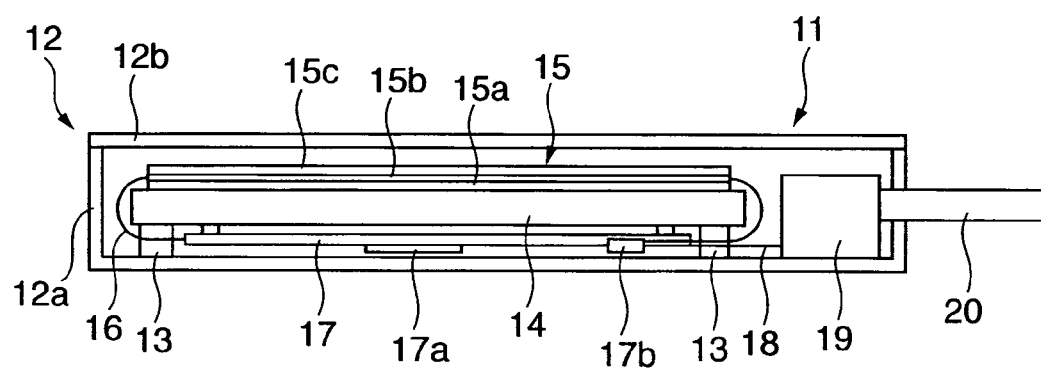
FIG. 1 is a sectional view of a radiographic image detection unit in the first embodiment.

FIG. 1 is a sectional view of a radiographic image detection unit 11. The radiographic image detection unit 11 can be used independently as a cassette, and can be used in combination with various holders. A housing cover 12b made of a material having high X-ray transmission covers the X-ray incident surface of a housing body 12a. The housing body 12a and the housing cover 12b constitute a sealed housing 12. A metal base 14 is fixed to the housing body 12a through a support portion 13. An X-ray detection panel 15 on which a board 15a, photoelectric conversion elements 15b, and fluorescent screen 15c are stacked is placed on the base 14.

As a material for the board 15a, a glass plate is often used because it has no chemical action with a semiconductor element, has high resistance to the temperature of a semiconductor process, has dimensional stability, and the like. The photoelectric conversion elements 15b are formed in a two-dimensional array on the board 15a by a semiconductor process. The fluorescent screen 15c is formed by coating a resin plate with a phosphor made of a metallic compound, and is integrated with the board 15a and the photoelectric conversion elements 15b with an adhesive.

Each photoelectric conversion element 15b connects, through a flexible circuit board 16 connected to a side surface of the photoelectric conversion element 15b, to a circuit board 17 which is placed on the lower surface of the base 14 and on which electronic parts 17a and 17b which process electrical signals obtained by photoelectric conversion are mounted. A relay electric circuit unit 19 connects to the circuit board 17 through a cable 18 and further connects to an external controller (not shown) through a cable 20 to perform power supply, signal transfer, and the like.

The radiographic image detection unit 11 having this arrangement can perform X-ray imaging by detecting X-rays emitted from an X-ray tube. More specifically, the X-rays emitted from the X-ray tube pass through a subject, and strike the radiographic image detection unit 11. The fluorescent screen 15c of the X-ray detection panel 15 then converts the X-rays into visible light. The photoelectric conversion elements 15b arranged in a two-dimensional array convert this visible light into an electrical signal, thereby obtaining a radiographic image signal. The digital radiographic image signal obtained by A/D conversion is transferred to an external controller 101 through the cable 20. The user can instantly observe the radiographic image on a monitor 103 connecting to the external controller 101.

The following reading scheme is used to read out electric charges from the X-ray detection panel 15. That is, a read circuit unit reads out, in the row direction, the electric charges accumulated by the electric conversion elements of the column selected by a driving circuit unit. When the radiographic image detection unit 11 having this arrangement is driven, the electronic parts 17a and 17b and the like generate heat while consuming power. The heat generated from the electronic parts 17a and 17b and the like raises the temperature inside the radiographic image detection unit 11 and radiates to the outer air through the housing 12.

Figure 2:
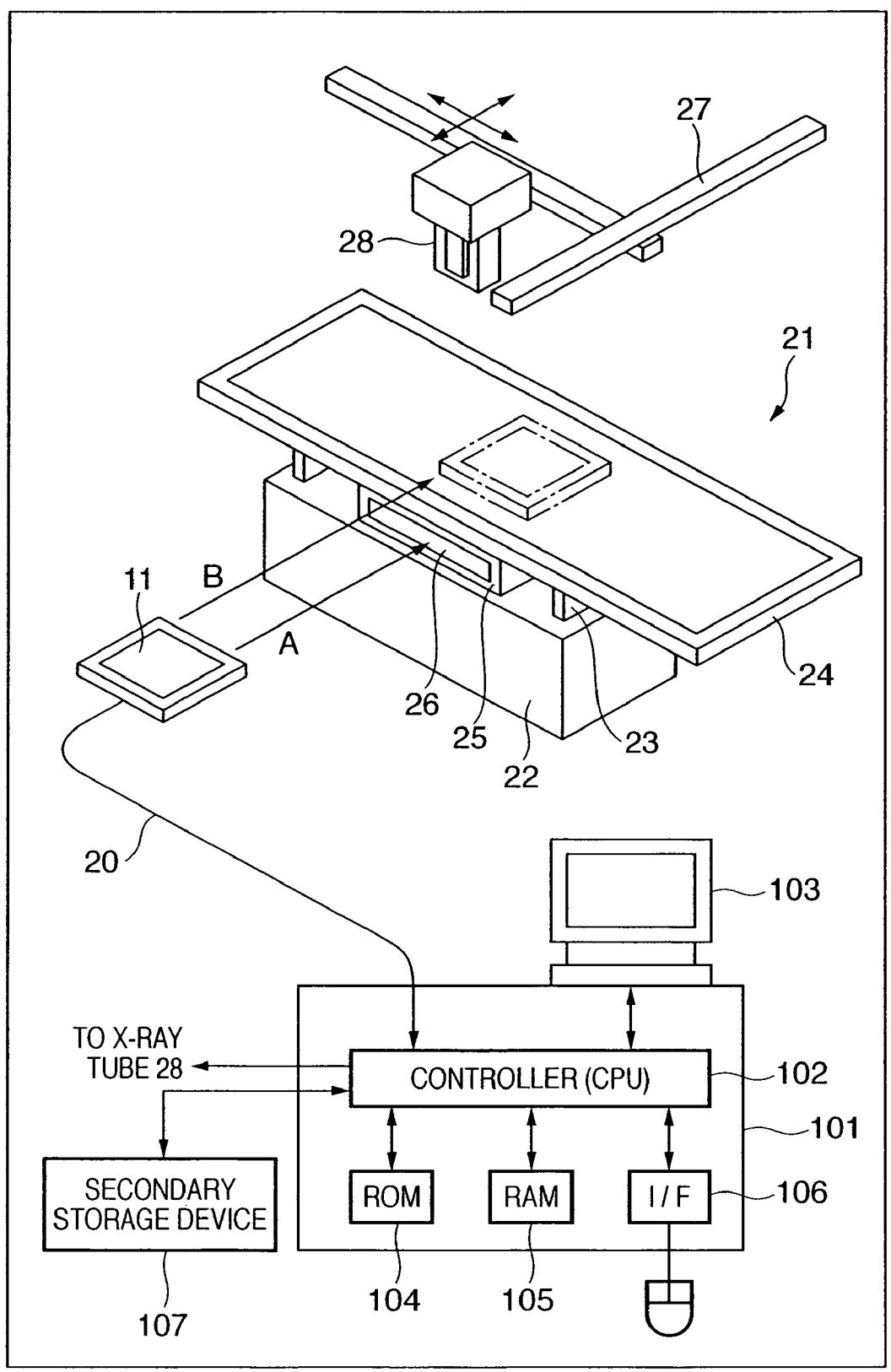
FIG. 2 is a view showing the arrangement of a radiographic apparatus.

FIG. 2 is a view showing the arrangement of the radiographic apparatus using a combination of the radiographic image detection unit 11, a radiographic stand 21, and the controller 101. The radiographic stand 21 has a top 24 which is supported through support portions 23 on a radiographic stand body 22 and on which a subject is placed. The support portions 23 support the top 24 so as to be movable within a horizontal plane.

A storage unit 25 for mounting the radiographic image detection unit 11 is provided between the radiographic stand body 22 and the top 24. The storage unit 25 is a support portion which permanently fixes the radiographic image detection unit 11. The storage unit 25 also functions as a cooling portion since it has a cooling mechanism to be described below. The front surface of the storage unit 25 has an opening portion 26 in which the radiographic image detection unit 11 is to be inserted. An X-ray tube 28 which can move along a guide portion 27 and applies X-rays is placed above the radiographic stand 21.

There are two methods of mounting the radiographic image detection unit 11 on the radiographic stand 21. One is the method of mounting the radiographic image detection unit 11 in the storage unit 25 as indicated by an arrow A. The other is the method of mounting the radiographic image detection unit 11 on the top 24 as indicated by an arrow B.

In the method indicated by the arrow A, which mounts the radiographic image detection unit 11 in the storage unit 25, since the subject does not directly come into contact with the radiographic image detection unit 11, the user can easily align the subject with the radiographic image detection unit 11. In contrast, in the method indicated by the arrow B, which mounts the radiographic image detection unit 11 on the top 24, the user can position the radiographic image detection unit 11 in various postures.

The controller 101 controls the radiographic image detection unit 11 and the X-ray tube 28 in accordance with the detection of mounting of the radiographic image detection unit 11 in the storage unit 25. In practice, the controller 101 controls the X-ray tube 28 through the X-ray generation unit and the X-ray generator. However, since a known technique can be applied to this control operation, a description will be omitted. The controller 101 includes a control unit 102, ROM 104, RAM 105, and I/F 106. The control unit 102 comprises a CPU and the like and comprehensively controls the overall controller 101. The ROM 104 is a computer-readable storage medium which stores programs for the execution of processing by the control unit 102. The RAM 105 is a temporary memory used for processing by the control unit 102. The I/F 106 is an interface which detects inputs from a pointing device such as a mouse or keyboard. The controller 101 connects to the monitor 103 for displaying a radiographic image or an operation window, and executes display control. A storage device 107 is a nonvolatile secondary storage device such as a hard disk drive device which stores the images output from the radiographic image detection unit 11.

Figure 3:
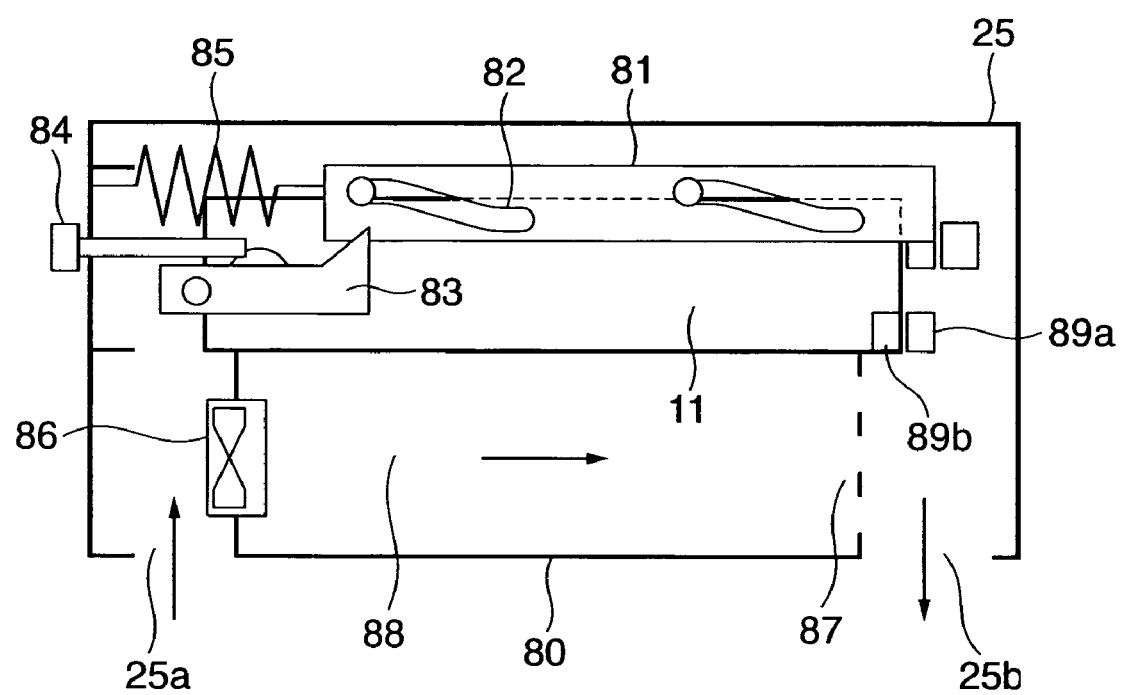
FIG. 3 is a view showing the arrangement of a cooling mechanism in the first embodiment.

FIG. 3 is a view showing the arrangement of a cooling mechanism used when the radiographic image detection unit 11 is mounted in the storage unit 25. A box-like frame member 80 having an open upper surface is provided in the storage unit 25.

When the radiographic image detection unit 11 is inserted into the storage unit 25 from the left in FIG. 3, the distal end of the radiographic image detection unit 11 abuts against a slide member 81 to push it deeply to the right. The slide member 81 is guided downward along a guide groove 82. Finally, the slide member 81 holds the radiographic image detection unit 11 so as to hold it in the opening portion of the frame member 80, and a lock portion 83 locks the slide member 81. With this operation, the radiographic image detection unit 11 is permanently supported. A detection member 89a is a member which is placed in the storage portion and comes into contact with a detector 89b when the radiographic image detection unit 11 is mounted in the storage unit 25. The detector 89b is placed on the radiographic image detection unit 11 and detects contact with the detection member 89a. Upon detecting this contact, the radiographic image detection unit 11 outputs a signal indicating that the radiographic image detection unit 11 is mounted in the controller 101. The detector 89b may be any sensor such as a pressure sensor.

When ejecting the radiographic image detection unit 11, the operator presses a switch 84 provided on the front surface of the storage unit 25 to move the lock portion 83 in the direction to release the slide member 81. A spring 85 then moves the slide member 81 to the left to eject the radiographic image detection unit 11.

A fan 86 and vents 87 are formed in side surfaces of the frame member 80. The fan 86 and the vents 87 are formed as a cooling mechanism by the radiographic image detection unit 11 and the frame member 80. The forced convection of an air layer on the rear surface side of the housing 12 dissipates the heat generated by the radiographic image detection unit 11. The storage unit 25 ventilates with the outside air through air holes 25a and 25b formed in the storage unit 25.

The radiographic image detection unit 11 generates heat when performing analog signal processing such as reading out electric charges from the X-ray detection panel 15 during radiography and performing digital signal processing such as image processing. The power consumed during radiography is larger than that consumed during standby. In addition, the average power consumption varies depending on radiographic intervals. That is, when radiography of a moving image is consecutively and repeatedly performed, the amount of heat generated greatly changes depending on the frame rate of radiographic images acquired per unit time.

When the radiographic image detection unit 11 is to be used singly, the heat dissipation of the radiographic image detection unit 11 is determined by heat dissipation performance from the outer jacket surface. In radiography of an moving image, however, there is a limit to heat dissipation based on only natural convection due to surface treatment or a heat dissipation surface. Therefore, a frame rate Fo which can be permitted in terms of heat dissipation performance is determined in advance.

Figure 4:
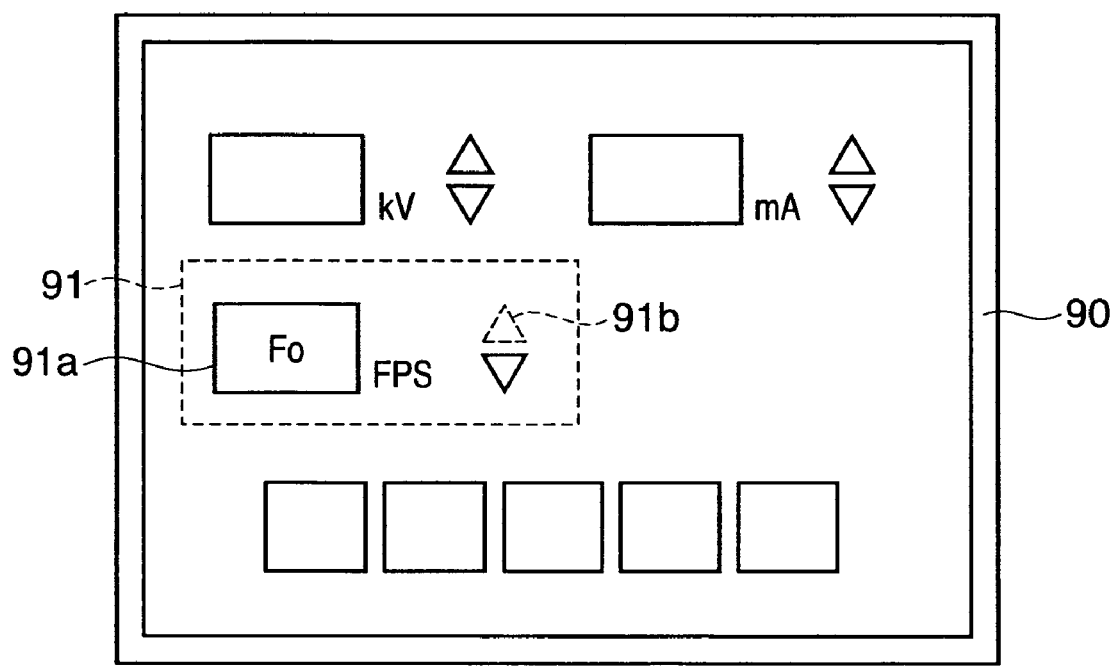
FIG. 4 is a view for explaining an operation window in the first embodiment.

FIG. 4 shows an operation window 90 which is displayed on the monitor 103 and allows the controller 101 to control the radiographic image detection unit 11 and the X-ray tube 28.

The upper area of the operation window 90 has setting areas for setting the tube voltage and tube current of the X-ray tube 28. An area 91 displays an operation object for setting a frame rate indicating the number of images to be acquired per unit time in radiography of a moving image.

A window display area 91a displays the value of a frame rate. Arrow keys 91b arranged as operation objects on a side of the window display area 91a allow issuing instructions to increase and decrease the frame rate. In this embodiment, when it is detected that the radiographic image detection unit 11 is mounted in the storage unit 25, the control unit 102 allows setting a frame rate up to a maximum frame rate Fu determined by the apparatus specifications. When it is not detected that the radiographic image detection unit 11 is mounted in the storage unit 25, the control unit 102 limits an allowable frame rate as an upper limit to a frame rate Fo lower than the maximum frame rate Fu. The control unit 102 then controls so as not to set a frame rate higher than the frame rate Fo even if the user selects the arrow key 91b. The control unit 102 performs display control to hide the arrow key 91b or change its color so as to notify the operator of the upper limit.

Figure 5:
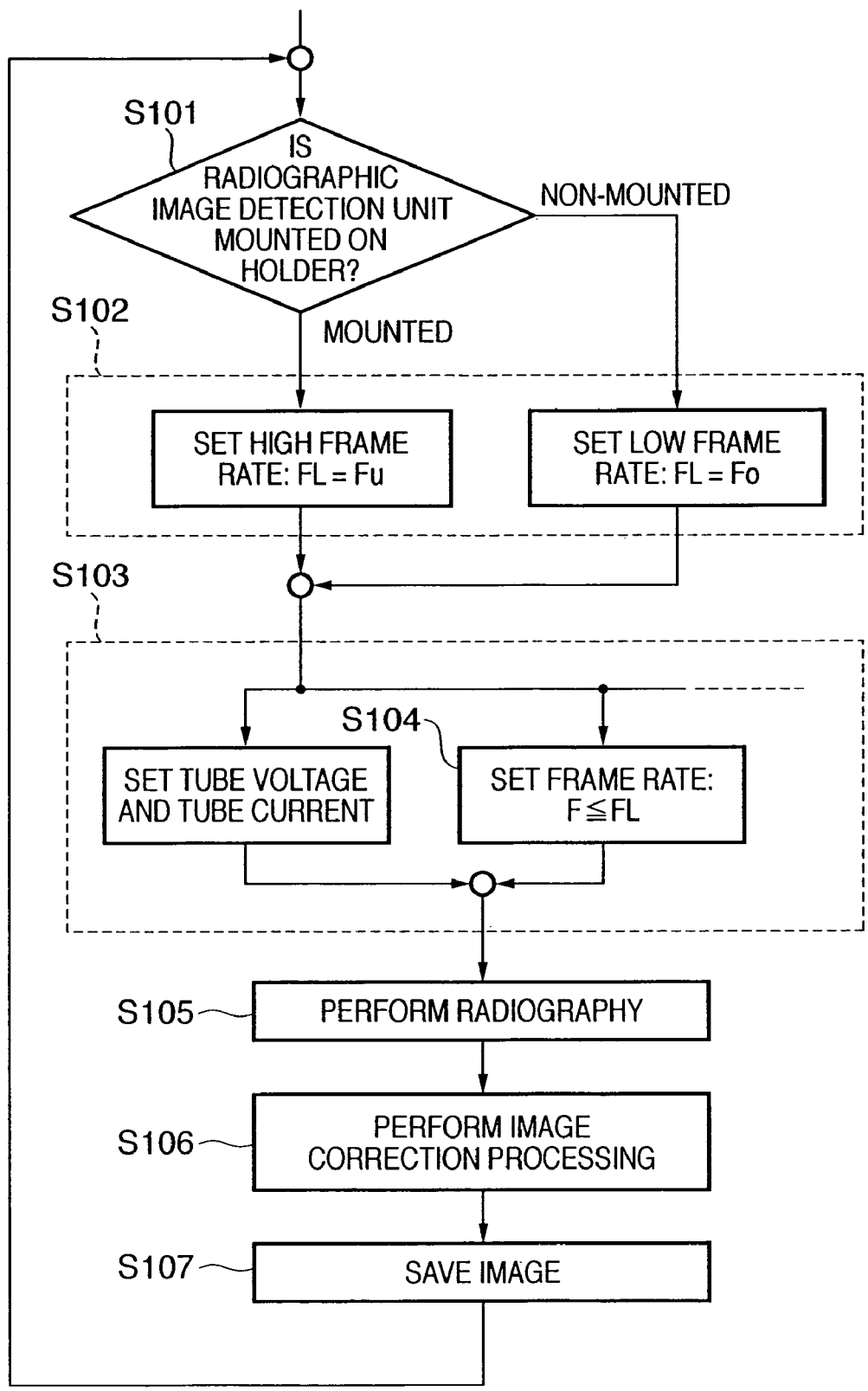
FIG. 5 is a flowchart for the operation of the first embodiment.

FIG. 5 is a flowchart showing operation processing executed by the control unit 102 of the controller 101.

First of all, in step S101, the control unit 102 determines based on a detection signal from the detector 89b of the radiographic image detection unit 11 whether the radiographic image detection unit 11 is mounted in the storage unit 25.

In step S102, if it is detected that the radiographic image detection unit 11 is mounted in the storage unit 25, the control unit 102 sets a maximum frame rate FL which can be set to the high frame rate Fu. If it is not detected that the radiographic image detection unit 11 is mounted in the storage unit 25, the control unit 102 limits the frame rate FL to the low frame rate Fo lower than Fu.

Step S103 is the step of setting radiographic conditions. For example, the control unit 102 sets the tube voltage and tube current of the X-ray tube which correspond to the input operation using the operation window shown in FIG. 4. In step S104, as one of processes of setting radiographic conditions, the control unit 102 sets a frame rate indicating the number of radiographic images output from the radiographic image detection unit per unit time in accordance with input operation using the operation window shown in FIG. 4. More specifically, the control unit 102 sets a frame rate by increasing/decreasing the frame rate value in accordance with detection of selection of the arrow key 91b in the operation window 90 in FIG. 4 by the user. The control unit 102 sets a frame rate F within a range including the maximum frame rate FL set in accordance with mounting of the radiographic image detection unit 11 as an upper limit. Upon detecting that a set value as an upper limit has been set by using the arrow key 91b, the control unit 102 controls to hide the arrow key 91b to inhibit the user from selecting any value equal to or more than the upper limit value.

When radiographic condition setting is complete in this manner, the control unit 102 controls the radiographic image detection unit 11 in step S105 to read out a radiographic image at the set frame rate. In addition, the control unit 102 instructs the X-ray tube 28 to control its tube voltage and tube current to those set in step S103. In addition, the control unit 102 controls the X-ray tube 28 to apply X-rays in synchronism with the frame rate set in step S104. In this manner, the control unit 102 controls radiography of radiographic images.

In step S106, the control unit 102 executes image correction processing such as tone conversion and the like with respect to the radiographic image output from the radiographic image detection unit 11, and displays the corrected radiographic image on the monitor 103.

In step S107, the control unit 102 causes the secondary storage device 107 to save the corrected radiographic image. The control unit 102 may perform the save processing in step S107 concurrently with step S106.

With the above arrangement of the radiographic apparatus, even when the radiographic image detection unit 11 is to be used singly, the apparatus can perform continuous radiography at a high frame rate which is made stable by the cooling mechanism at the time of mounting of the radiographic image detection unit 11 on the holder without any influence on the operation performance based on compactness and light-weightness. If the radiographic image detection unit 11 is not permanently supported by the storage unit 25, since processing for restricting radiography of a moving image is executed, safety improves.

Second Embodiment

Figure 8:
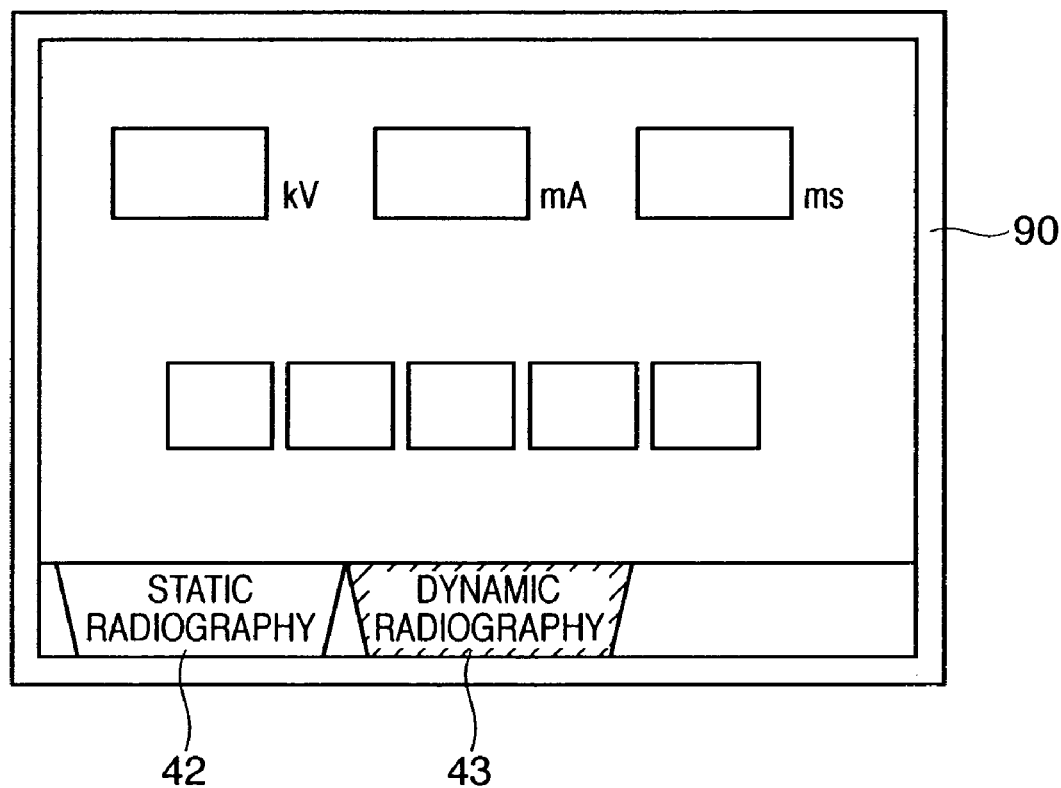
FIG. 8 is a view for explaining an operation window in the second embodiment.

The operation processing by a cooling mechanism and a controller 101 according to the second embodiment will be described next. FIG. 8 shows an operation window 90 displayed on a monitor 103 in the second embodiment.

Figure 6:
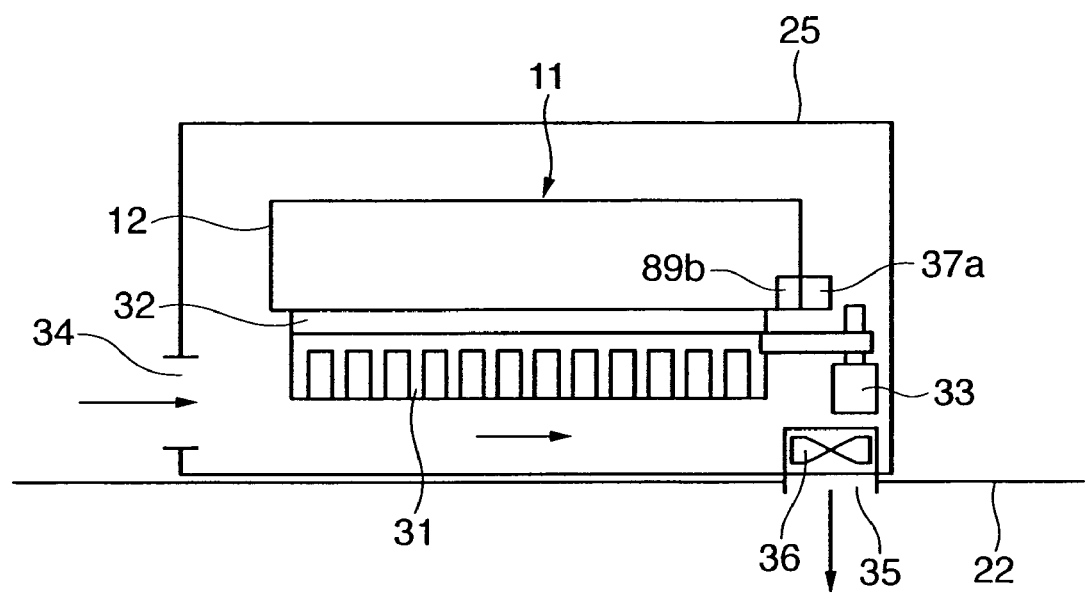
FIG. 6 is a view showing the arrangement of a cooling mechanism in the second embodiment.

FIG. 6 is a sectional view showing the cooling mechanism in a storage unit 25 according to the second embodiment. FIG. 6 shows a state wherein a radiographic image detection unit 11 is mounted in the storage unit 25.

The storage unit 25 houses a cooling mechanism comprising a heat dissipation fin 31 and heat dissipation rubber 32. An actuator 33 which is provided on a side of this cooling mechanism so as to be in contact with the mounted radiographic image detection unit 11 supports the cooling mechanism so as to allow it to be vertically movable. A side surface of the storage unit 25 has an opening portion 34 for intaking air. The bottom surface of the storage unit 25 has an opening portion 35 communicating with a radiographic stand body 22. A blower fan 36 for forcibly sending air is placed near the opening portion 35. The storage unit 25 houses a detection member 37a for detecting that the radiographic image detection unit 11 is mounted at a predetermined position inside the storage unit 25. As described above, a detector 89b is provided in the radiographic image detection unit 11, and detects contact with the detection member 37a to detect that the radiographic image detection unit 11 is mounted at a predetermined position inside the storage unit 25.

When it is detected that the radiographic image detection unit 11 is mounted at the predetermined position inside the storage unit 25, the actuator 33 starts driving. The actuator 33 then brings the cooling mechanism into contact with the back surface of the radiographic image detection unit 11 to form a new heat transfer path.

The heat generated by the radiographic image detection unit 11 is therefore dissipated from the opening portion 35 toward the radiographic stand body 22 by the blower fan 36 through the path formed by a housing 12, the heat dissipation rubber 32, and the heat dissipation fin 31.

Upon receiving an input signal from an attachment/detachment instruction unit (not shown) when the user removes the radiographic image detection unit 11, the actuator 33 moves the cooling mechanism downward and separates it from the back surface of the radiographic image detection unit radiographic image detection unit 11.

Figure 7:
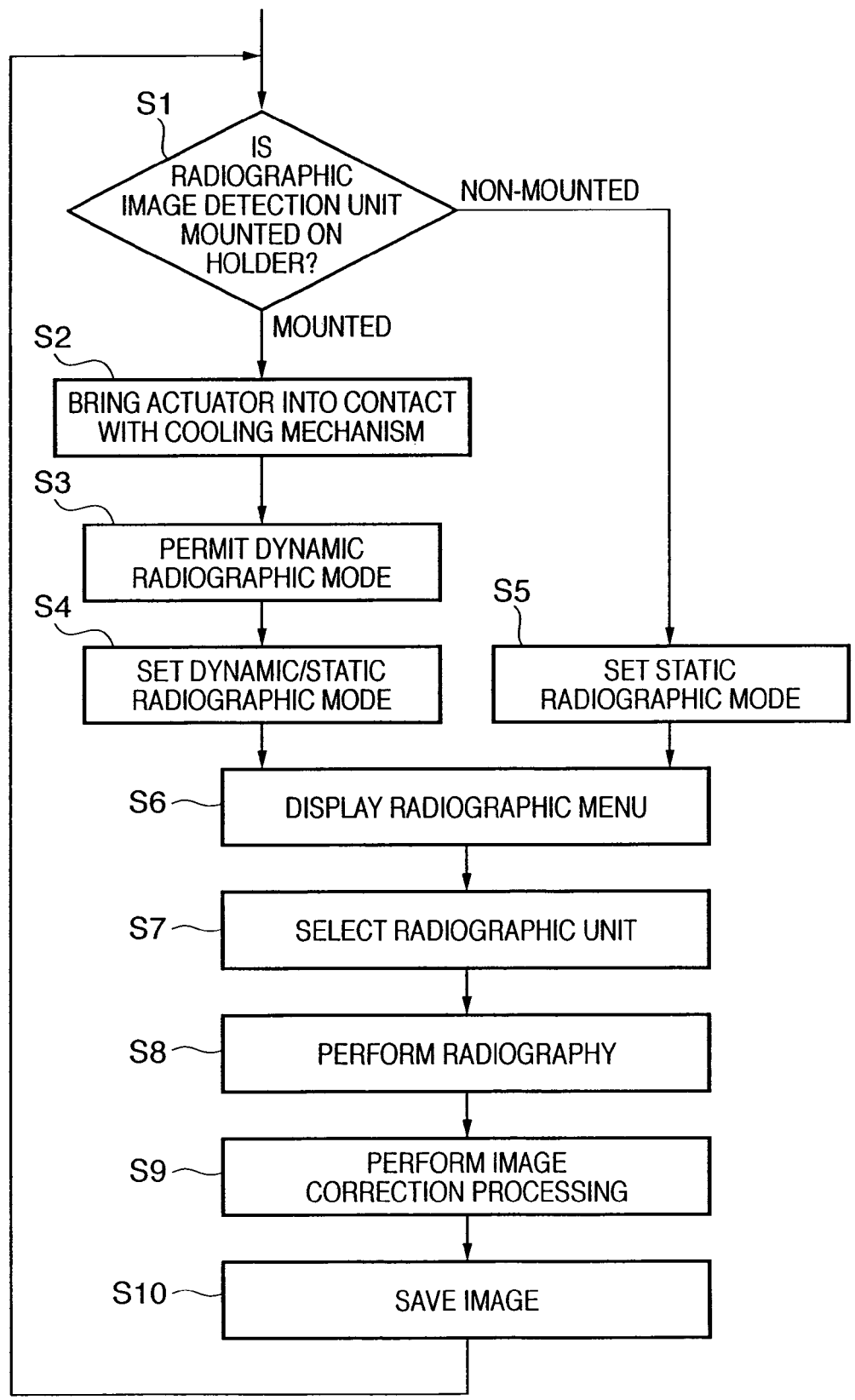
FIG. 7 is a flowchart for the operation of the second embodiment.

FIG. 7 is a flowchart showing the operation processing executed by a control unit 102 of the controller 101.

First of all, in step S1, the control unit 102 determines based on the presence/absence of a detection signal from a detector 39b whether the radiographic image detection unit 11 is mounted in the storage unit 25. If the control unit 102 receives a detection signal from the detector 39b and determines that the radiographic image detection unit 11 is mounted in the storage unit 25, the process shifts to step S2. The control unit 102 controls the actuator 33 to come into contact with the cooling mechanism comprising the heat dissipation fin 31 and the heat dissipation rubber 32. Note that in this embodiment, as indicated by step S3, the controller 101 having the control unit 102 may output an instruction to control the actuator 33 to the storage unit 25. As another example of operation, it suffices to perform the following operation. The detection member 37a has a function as a sensor. The detection member 37a detects the contact of the radiographic image detection unit 11. The actuator 33 then operates without through the controller 101 to bring the cooling mechanism into contact with the radiographic image detection unit 11 in accordance with the detection. The processing in step S2 makes the cooling mechanism come into contact with the back surface of the radiographic image detection unit 11 to improve the cooling performance.

In step S3, when receiving a detection signal from the detector 39b and determining that the radiographic image detection unit 11 is mounted in the storage unit 25, the control unit 102 permits the execution of radiography in a radiographic mode for obtaining a moving image.

In step S4, the control unit 102 detects the selection of the modes for obtaining a moving or still image by the user through the operation window 90 shown in FIG. 8, and sets the detected radiographic mode. Note that the radiographic mode for obtaining a still image is the mode of capturing one radiographic image with respect to one emission input instruction, and the radiographic mode for obtaining a moving image is the mode of performing continuous radiography.

In step S1, when the control unit 102 receives no detection signal from the detector 39b and determines that the radiographic image detection unit 11 is not mounted in the storage unit 25, the process advances to step S5. The control unit 102 sets the radiographic mode for obtaining a still image. That is, the control unit 102 imposes restriction on radiography in the radiographic mode for obtaining a moving image.

Note that in the radiographic mode for obtaining a still image, the control unit 102 repeats twice electric charge accumulation for about one sec at most and read operation for about one sec at most except for a special case. This operation is performed to acquire a radiographic image and a correction image.

In general, one subject is made to change his/her posture or subjects are changed one after another. In the radiographic mode for obtaining a still image, therefore, the radiographic intervals are several 10's of seconds at the shortest, and radiography does not continue for a long period of time. In contrast, in the radiographic mode for obtaining a moving image in this embodiment, it is a premise that 30 images are acquired per second. When radiography of a moving image is executed for several minutes, the amount of heat generated rapidly increases as compared with the radiographic mode for obtaining a still image.

In step S6, the control unit 102 displays a menu corresponding to the radiographic mode set in step S4 or S5 in the operation window 90 on the monitor 103. In step S7, the control unit 102 detects the selection of a detection region by the user. The operation window 90 shown in FIG. 8 displays tags 42 and 43 for the selection of the radiographic modes. Upon detecting the selection of the tag 42 for radiography of a still image, the control unit 102 displays the setting state of the tube voltage and tube current of the X-ray tube and selection icons such as a radiographic region in correspondence with radiography of a still image. Upon detecting the selection of an icon in the operation window 90 shown in FIG. 8, the control unit 102 sets radiographic conditions corresponding to the selected desired region.

Upon detecting the selection of the tag 43 for obtaining radiography of a moving image, the control unit 102 displays an operation window corresponding to radiography of a moving image. The operation window corresponding to radiography of a moving image displays an operation menu for radiography of a moving image such as setting of a frame rate and the like in addition to the operation window shown in FIG. 8.

Upon determining in step S1 that the radiographic image detection unit 11 is not mounted in the storage unit 25, the control unit 102 controls to hide the tag 43. This can limit the mode in which radiography can be performed. That is, when the radiographic image detection unit 11 is mounted in the storage unit 25, the tag 43 for radiography of a moving image is displayed. When the detection unit is to be used singly, the tag 43 for radiography of a moving image is hidden.

In step S8, the control unit 102 controls the radiographic image detection unit 11 and the X-ray tube 28 to execute radiography under the set radiographic conditions.

In step S9, the control unit 102 executes image correction processing such as tone conversion processing with respect to the radiographic image output from the radiographic image detection unit 11, and displays the corrected radiographic image on the monitor 103.

In step S10, the control unit 102 causes the secondary storage device 107 to save the corrected radiographic image.

In step S10, the control unit 102 may perform the save processing in step S10 concurrently with step S9.

The above arrangement of the radiographic apparatus can prevent the service life of the radiographic image detection unit 11 from being shortened.

Third Embodiment

Figure 9:
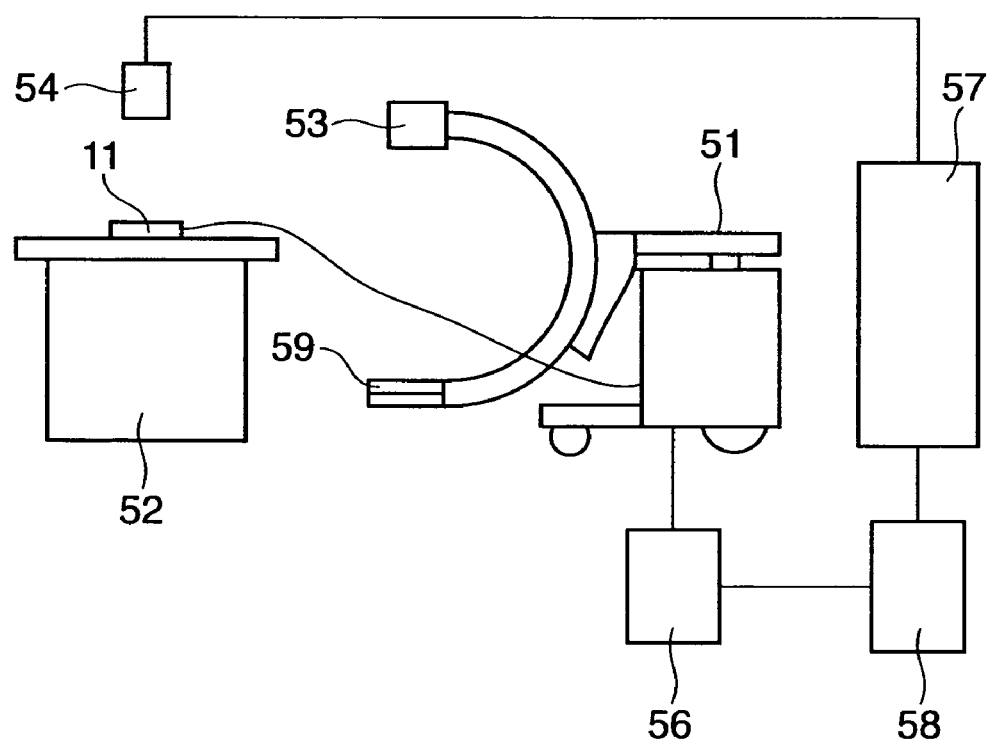
FIG. 9 is a view showing the arrangement of a radiographic apparatus according to the third embodiment.

FIG. 9 is a view showing the arrangement of a radiographic apparatus according to the third embodiment. In the third embodiment, X-ray tubes 53 and 54 are mounted on a movable C-arm device 51 and a radiographic stand 52, respectively. In this case, the user prepares for radiography by mounting the radiographic image detection unit 11 on the C-arm device 51 or radiographic stand 52.

The distal end of the arm of the C-arm device 51 has a mount portion 59 for detachably supporting a radiographic image detection unit 11. The mount portion 59 has a cooling mechanism for cooling a radiographic image detection unit 55 as in the second embodiment. The radiographic image detection unit 11 acquires a radiographic image by detecting X-rays applied from the X-ray tube 53.

A controller 56 connects to the C-arm device 51. The controller 56 has functions similar to those in the first and second embodiments. The C-arm device 51 is mainly used for radiography of a moving image such as fluoroscopic radiography.

The controller 56 also connects to an X-ray generation control unit 58, and can control the X-ray tube 54 different from the X-ray tube 53 mounted on the C-arm device 51. Although not shown in FIG. 2, the X-ray generation control unit 58 controls the generation of X-rays based on instructions from the controller. An X-ray generator 57 controls the X-ray tube 54 at the timing instructed by the X-ray generation control unit 58. In this case, removing the radiographic image detection unit 11 from the C-arm device 51 and placing it on the radiographic stand 52 can perform radiography of a still image.

The controller 56 monitors the mounted/non-mounted state of the radiographic image detection unit 11 on the mount portion 59 of the C-arm device 51. Upon determining from an output from the detection sensor of the mount portion 59 that the radiographic image detection unit 11 is mounted, the controller 56 activates the C-arm device 51 and displays an operation window for operating the C-arm device 51 on a monitor (not shown) connecting to the controller 56. If the radiographic image detection unit 11 is not mounted on the mount portion 59, the controller 56 displays an operation window for setting a tube voltage and a tube current for the X-ray tube 54 on a monitor (not shown). Setting in advance operation windows for the X-ray tube 54 as operation windows for radiography of a still image makes it possible to have the same functions as those of the second embodiment.

(Cooling Mechanism and Another Form)

Figure 10:
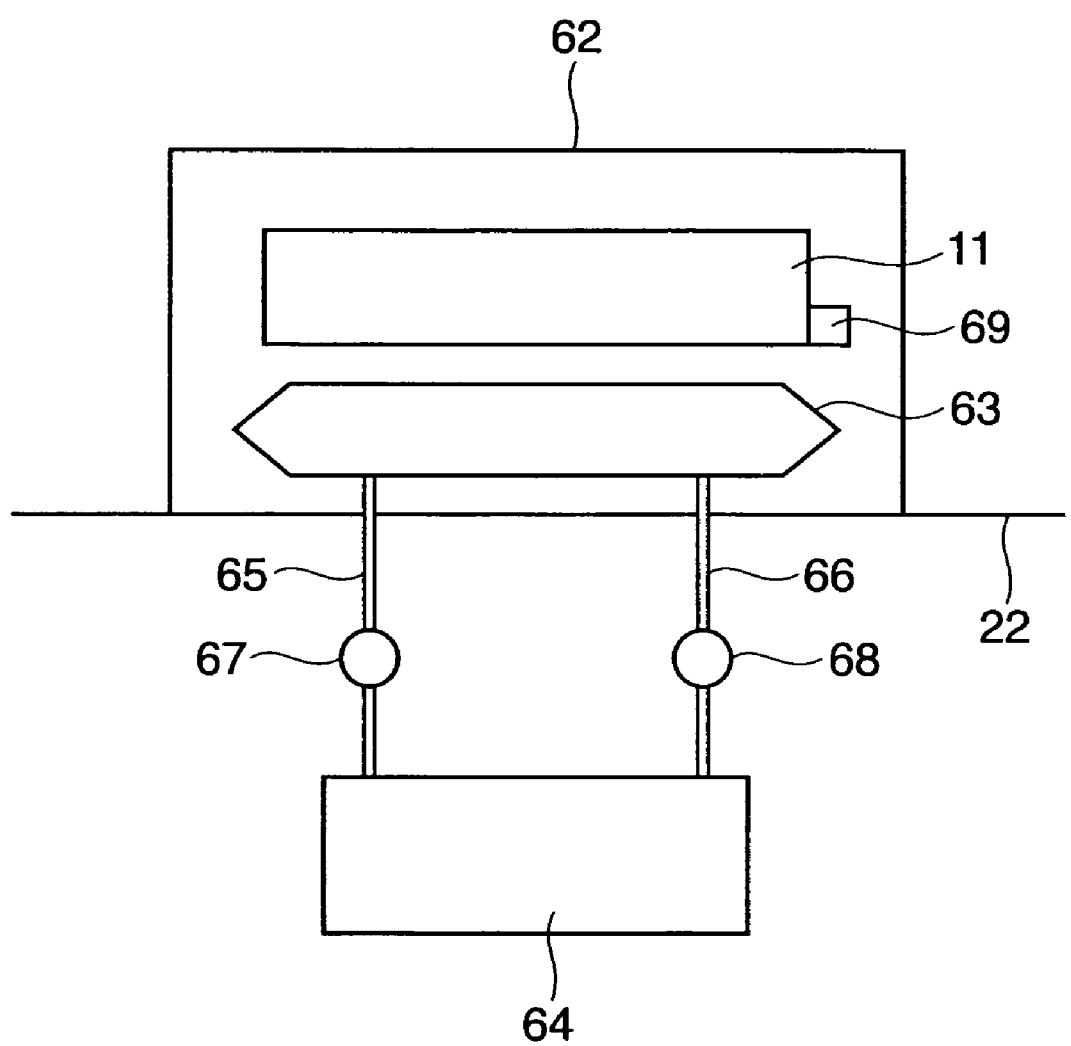
FIG. 10 is a view showing the arrangement of another form of the cooling mechanism.
Figure 11:
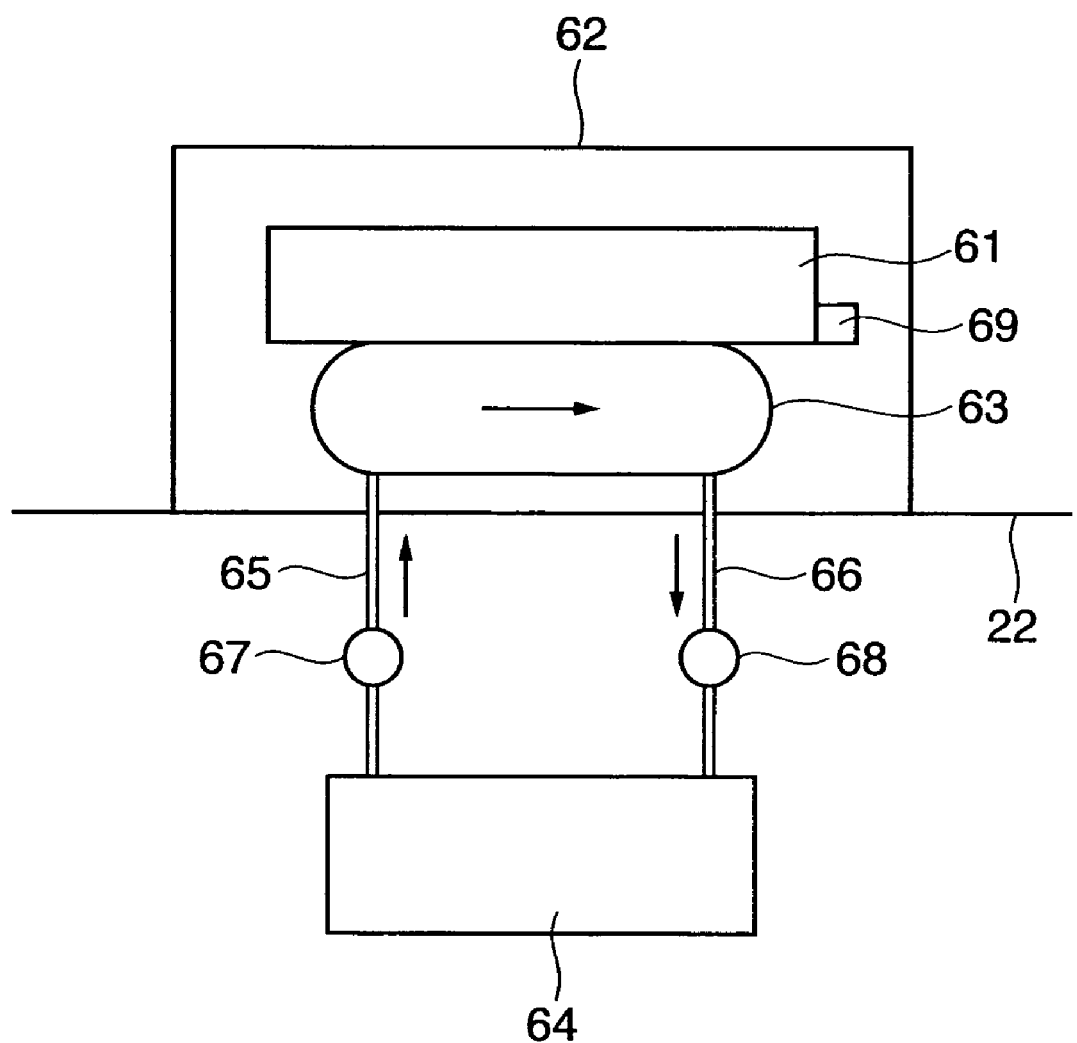
FIG. 11 is a view showing the arrangement of the form of the cooling mechanism shown in FIG. 10.

FIGS. 10 and 11 show another form of the cooling mechanism which can be applied to the first and second embodiments in a state wherein the radiographic image detection unit is separate from the cooling mechanism. This cooling mechanism is connectable interlockingly with attachment/detachment of the radiographic image detection unit 11.

A storage portion 62 houses a cooling bag 63 filled with a cooling liquid medium functioning as a cooling mechanism. A tank 64 also serving as a heat dissipation portion for the cooling medium is provided outside the storage portion 62. The tank 64 is provided inside a radiographic stand body 22.

The cooling bag 63 connects to the tank 64 through tubes 65 and 66, which respectively serve as supply and discharge tubes for the cooling bag 63. Two independent pumps 67 and 68 are respectively provided for the tubes 65 and 66.

Before a radiographic image detection unit 11 is mounted in the storage portion 62, the cooling bag 63 is at a position away from the radiographic image detection unit 11, as shown in FIG. 10 (for the sake of descriptive convenience, FIG. 10 shows a state wherein the radiographic image detection unit 11 is mounted). When the radiographic image detection unit 11 is mounted and a detector 69 detects that the unit is mounted at a predetermined position, the supply pump 67 operates to fill the cooling bag 63 with the cooling medium. The cooling bag 63 then expands. When coming into contact with the back surface of the radiographic image detection unit 11, the cooling bag 63 effectively functions as a cooling mechanism.

When the cooling bag 63 sufficiently expands and the inner pressure exceeds a predetermined pressure, the pump 68 starts driving to circulate the cooling medium to equalize the flow rates of the two pumps 67 and 68 so as to maintain the shape of the cooling bag 63. The heat generated by the radiographic image detection unit 11 is transferred by the cooling medium and is dissipated outside through a heat dissipation fin (not shown) provided on the surface of the tank 64.

When the radiographic image detection unit 11 is to be removed from the storage portion 62, control is performed to make the flow rate of the discharge pump 68 higher than that of the supply pump 67 in accordance with a signal from an attachment/detachment unit (not shown). This reduces the cooling medium in the cooling bag 63. As a consequence, the cooling bag 63 itself contracts and separates from the back surface of the radiographic image detection unit 11.

(Another Form of Radiographic Image Detection Unit)

Figure 12:
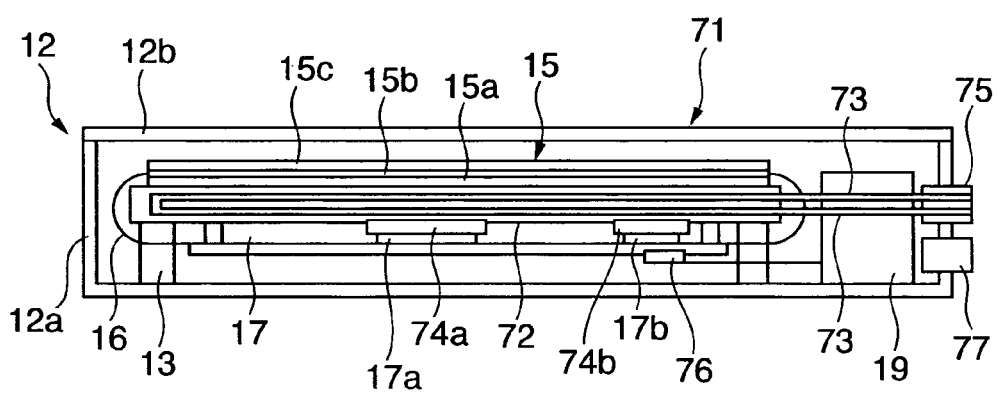
FIG. 12 is a sectional view of another radiographic image detection unit.
Figure 13:
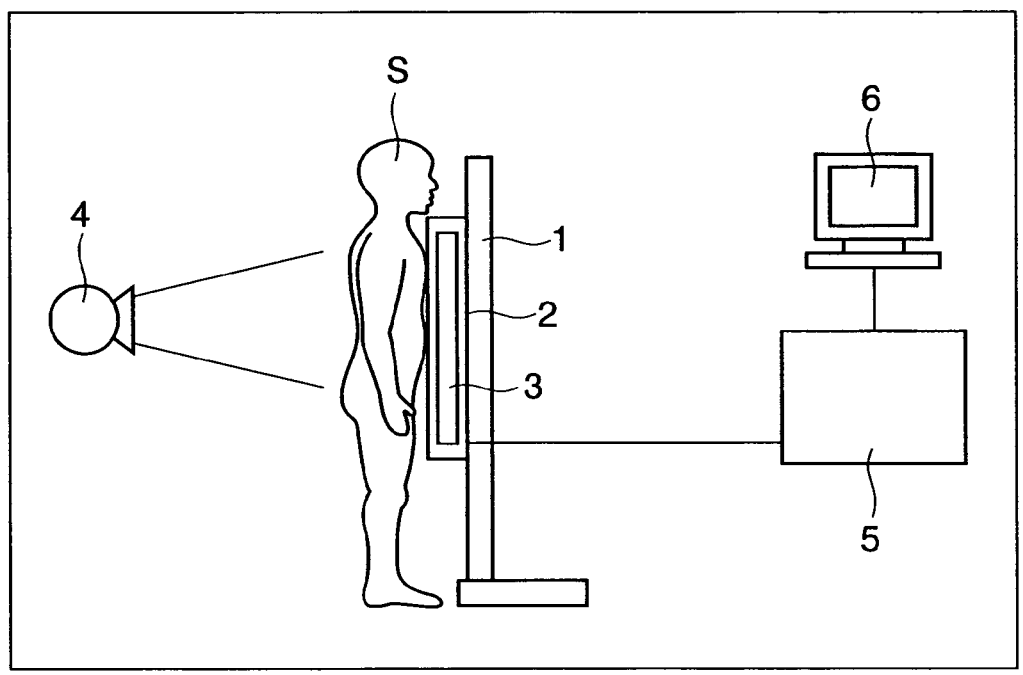
FIG. 13 is a view showing the arrangement of a conventional radiographic system.

FIG. 12 shows another form of the radiographic image detection unit. FIG. 12 is a sectional view of a radiographic image detection unit 71. The same reference numerals as those of the members of the radiographic image detection unit 11 in FIG. 1 denote the same members in FIG. 12. The radiographic image detection unit 71 incorporates a cooling mechanism.

A base 72 in the radiographic image detection unit 71 has a pipe member 73 for circulating a cooling medium. A circuit board 17 which processes a photoelectrically converted electrical signal connects to a flexible circuit board 16, and is fixed on the lower surface side of the base 72. Electronic parts 17a and 17b on the circuit board 17 are arranged on the base 72 side. A cooling mechanism is formed for the base 72 through heat dissipation rubber 74a and heat dissipation rubber 74b. A coupling 75 for the pipe member 73 for circulating the cooling medium is provided on a side surface of the housing body 12a, and connects to an external cooling medium circulating unit (not shown).

The circuit board 17 connects to a relay electric circuit unit 19 through a connector 76. The relay electric circuit unit 19 connects to a connector 77 for external connection. The relay electric circuit unit 19 connects to a connector 77 for external connection, through which power supply and signal transfer are performed. When cassette radiography is to be performed singly, operating a battery circuit and wireless circuit provided for the relay electric circuit unit 19 makes it possible to wirelessly communicate with the outside world.

The preferred embodiments of the present invention have been described above. Obviously, however, the present invention is not limited to these embodiments. The embodiments can be variously modified and changed within the spirit and scope of the invention.

In particular, a holder to be combined with these embodiments is not limited to a radiographic stand. For example, each embodiment can comprise an upright stand, universal stand, or the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-188863, filed Jul. 10, 2006, and Japanese Patent Application No. 2007-141491, filed May 29, 2007, which are hereby incorporated by reference herein in their entirety.

The invention claimed is:

1. A radiographic apparatus comprising:
   a mount detection unit which detects whether a radiographic image detection unit for acquiring a radiographic image is mounted on a cooling portion for cooling the radiographic image detection unit; and
   a controller which executes processing for restricting radiography of a moving image by the radiographic image detection unit when said mount detection unit does not detect mounting of the radiographic image detection unit on the cooling portion,
   wherein said controller restricts a frame rate of the moving image by the radiographic image detection unit more when said mount detection unit does not detect mounting of the radiographic image detection unit on the cooling portion than when said mount detection unit detects mounting of the radiographic image detection unit.

2. The apparatus according to claim 1, wherein a cooling mechanism for cooling the radiographic image detection unit comes into contact with the radiographic image detection unit in accordance with detection of mounting of the radiographic image detection unit by said mount detection unit.

3. A control method for a radiographic apparatus, comprising the steps of:
   detecting whether a radiographic image detection unit for acquiring a radiographic image is mounted on a support portion for supporting the radiographic image detection unit; and
   executing processing for restricting radiography of a moving image by the radiographic image detection unit when said detecting step does not detect mounting of the radiographic image unit on the support portion,
   wherein said executing processing step includes restricting a frame rate of the moving image by the radiographic image detection unit more when mounting of the radiographic image detection unit on the support portion is not detected in said detecting step than when mounting of the radiographic image detection unit is detected in said detecting step.

4. A control method for a radiographic apparatus, comprising the steps of:
   detecting whether a radiographic image detection unit for acquiring a radiographic image is mounted on a cooling portion for cooling the radiographic image detection unit; and
   executing processing for restricting radiography of a moving image by the radiographic image detection unit when said detecting step does not detect mounting of the radiographic image detection unit on the cooling portion,
   wherein said executing processing step includes restricting a frame rate of the moving image by the radiographic image detection unit more when mounting of the radiographic image detection unit on the cooling portion is not detected in said detecting step than when mounting of the radiographic image detection unit is detected in said detecting step.

5. A radiographic apparatus comprising:
a mount detection unit which detects whether a radiographic image detection unit for acquiring a radiographic image is mounted on a support portion for supporting said radiographic image detection unit; and
a controller which executes processing for restricting radiography of a moving image by the radiographic image detection unit when said mount detection unit does not detect mounting of the radiographic image detection unit on the support portion,
wherein said controller restricts a frame rate of the moving image by the radiographic image detection unit more when said mount detection unit does not detect mounting of the radiographic image detection unit on the support portion than when said mount detection unit detects mounting of the radiographic image detection unit.

6. The apparatus according to claim 5, wherein said controller restricts display of an operation window for execution of radiography of the moving image as radiography by the radiographic image detection unit, which is displayed on a monitor, when said mount detection unit does not detect mounting of the radiographic image detection unit on the support portion.

7. A radiographic apparatus comprising:
a mount detection unit which detects whether a radiographic image detection unit for acquiring a radiographic image is mounted on a support portion for supporting said radiographic image detection unit; and
a controller which executes processing for restricting radiography of a moving image by the radiographic image detection unit when said mount detection unit does not detect mounting of the radiographic image detection unit on the support portion,
wherein said controller controls display of an operation window for setting a frame rate which is displayed on a monitor so as to limit the frame rate when said mount detection unit does not detect mounting of the radiographic image detection unit on the support portion.

* * * * *